(12) United States Patent
Zhou

(10) Patent No.: US 10,342,247 B2
(45) Date of Patent: Jul. 9, 2019

(54) SUGAR COMPOSITIONS FOR TABLETING BY DIRECT COMPRESSION

(71) Applicant: ROQUETTE FRERES, Lestrem (FR)

(72) Inventor: Liuming Zhou, Geneva, IL (US)

(73) Assignee: ROQUETTE FRERES, Lestrem (FR)

( * ) Notice: Subject to any disclaimer, the term of this patent is extended or adjusted under 35 U.S.C. 154(b) by 131 days.

(21) Appl. No.: 15/327,556

(22) PCT Filed: Jul. 16, 2015

(86) PCT No.: PCT/IB2015/001303
§ 371 (c)(1),
(2) Date: Jan. 19, 2017

(87) PCT Pub. No.: WO2016/012854
PCT Pub. Date: Jan. 28, 2016

(65) Prior Publication Data
US 2018/0206538 A1    Jul. 26, 2018

(30) Foreign Application Priority Data
Jul. 21, 2014    (EP) .................................... 14306180

(51) Int. Cl.
| | | |
|---|---|---|
| A23L 5/00 | (2016.01) | |
| A61K 9/20 | (2006.01) | |
| A23L 21/00 | (2016.01) | |
| A23L 27/30 | (2016.01) | |
| A23L 29/30 | (2016.01) | |
| A23L 33/10 | (2016.01) | |
| A23P 10/20 | (2016.01) | |
| A23P 10/25 | (2016.01) | |
| A23P 10/28 | (2016.01) | |
| A23L 33/125 | (2016.01) | |
| A61K 31/7004 | (2006.01) | |

(52) U.S. Cl.
CPC ................. *A23L 27/33* (2016.08); *A23L 5/00* (2016.08); *A23L 21/00* (2016.08); *A23L 29/30* (2016.08); *A23L 33/10* (2016.08); *A23L 33/125* (2016.08); *A23P 10/20* (2016.08); *A23P 10/25* (2016.08); *A23P 10/28* (2016.08); *A61K 9/20* (2013.01); *A61K 9/2054* (2013.01); *A61K 9/2095* (2013.01); *A61K 31/7004* (2013.01); *A23V 2002/00* (2013.01)

(58) Field of Classification Search
None
See application file for complete search history.

(56) References Cited

U.S. PATENT DOCUMENTS

| | | |
|---|---|---|
| 2009/0068710 A1† | 3/2009 | Izumori |
| 2009/0304891 A1 | 12/2009 | Fujijara et al. |
| 2010/0129865 A1† | 5/2010 | Maruta |
| 2010/0173859 A1† | 7/2010 | Kolter |
| 2010/0204346 A1† | 8/2010 | Okuma |
| 2011/0112043 A1† | 5/2011 | Izumori |
| 2011/0237790 A1 | 9/2011 | Lee et al. |
| 2012/0076908 A1 | 3/2012 | Fujijara et al. |
| 2014/0370171 A1 | 12/2014 | Takaoka et al. |

FOREIGN PATENT DOCUMENTS

| | | | |
|---|---|---|---|
| CN | 101177672 A | | 5/2008 |
| CN | 102697744 A | | 10/2012 |
| CN | 103333935 A | | 10/2013 |
| EP | 1 538 200 A1 | | 6/2005 |
| EP | 1 860 195 A1 | | 11/2007 |
| EP | 1 905 442 A1 | | 4/2008 |
| EP | 2 156 751 A1 | | 2/2010 |
| JP | 2001-11090 A | | 1/2001 |
| JP | 2005-263670 A | | 9/2005 |
| JP | 2011-205913 A | | 10/2011 |
| WO | 2005/060937 A1 † | | 7/2005 |
| WO | 2013/103106 A1 | | 7/2013 |

OTHER PUBLICATIONS

Fuji, Fuji Chemical Industry, Pharmaceutical Technical Newsletter, Issue 20: Sep. 2010.*
Database WPI Week 200873, Thomson Scientific, London, GB; AN 2008-M34523, XP002734116.
Database WPI Week 201419, Thomson Scientific, London, GB; AN 2013-W83277, XP002734117.
Database WPI Week 201175, Thomson Scientific, London, GB; AN 2011-N75570, XP002734118.
Database WPI Week 201348, Thomson Scientific, London, GB; AN 2013-L75969, XP002734119.
G.K. Dokala, et al.: "Direct Compression—An Overview", International Journal of Research in Pharmaceutical and Biomedical Sciences, vol. 4, No. 1, 2013, pp. 155-158.
International Search Report, dated Dec. 1, 2015, from corresponding PCT Application.
Mar. 9, 2019 Office Action issued in Chinese Application No. 201580039823.8.
Li et al., "The application of factor analysis to evaluate deforming behaviors of directly compressed powders", pp. 47-57, pub'd Jul. 12, 2013, Powder Technology 247.†
Mu et al., "Recent advances on applications and biotechnological production of D-psicose", pp. 1461-1467, pub'd May 10, 2012, Appl. Microbiol. Biotechnol. 94.†

* cited by examiner
† cited by third party

*Primary Examiner* — Layla D Berry
(74) *Attorney, Agent, or Firm* — Oliff PLC

(57) ABSTRACT

Directly compressible compositions that include more than 30% by weight of allulose, and tablets obtainable thereof.

26 Claims, 2 Drawing Sheets

Figure 1: Compressibility and Ejection force of compositions comprising allulose
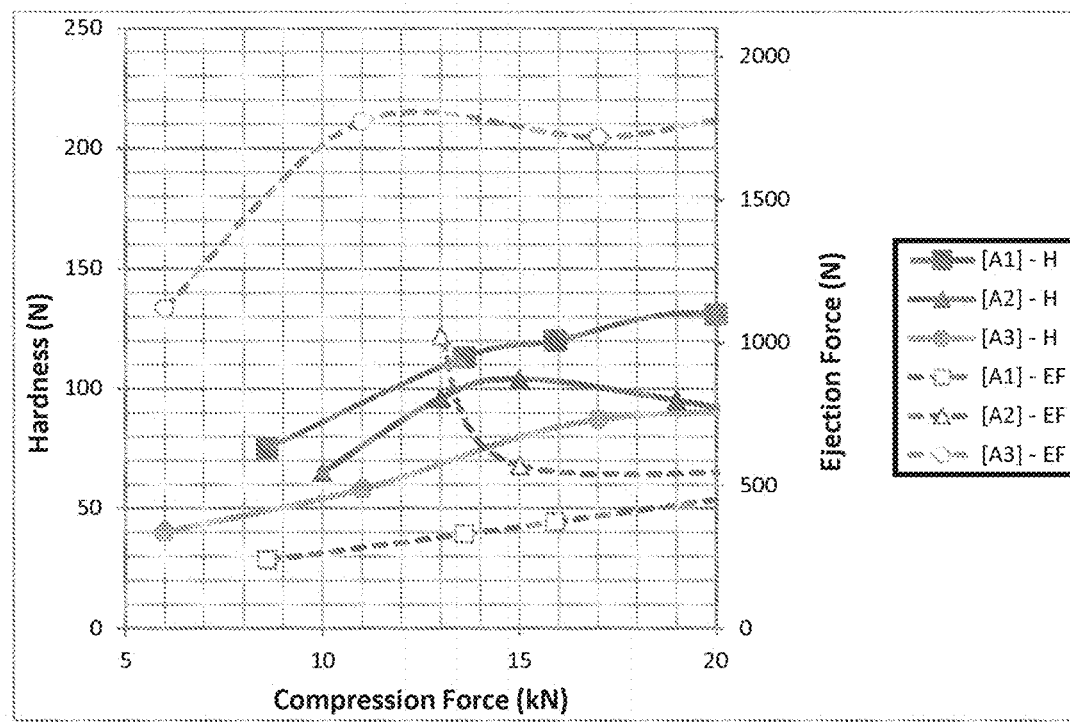
Figure 2: Compressibility and Ejection force of compositions comprising xylitol
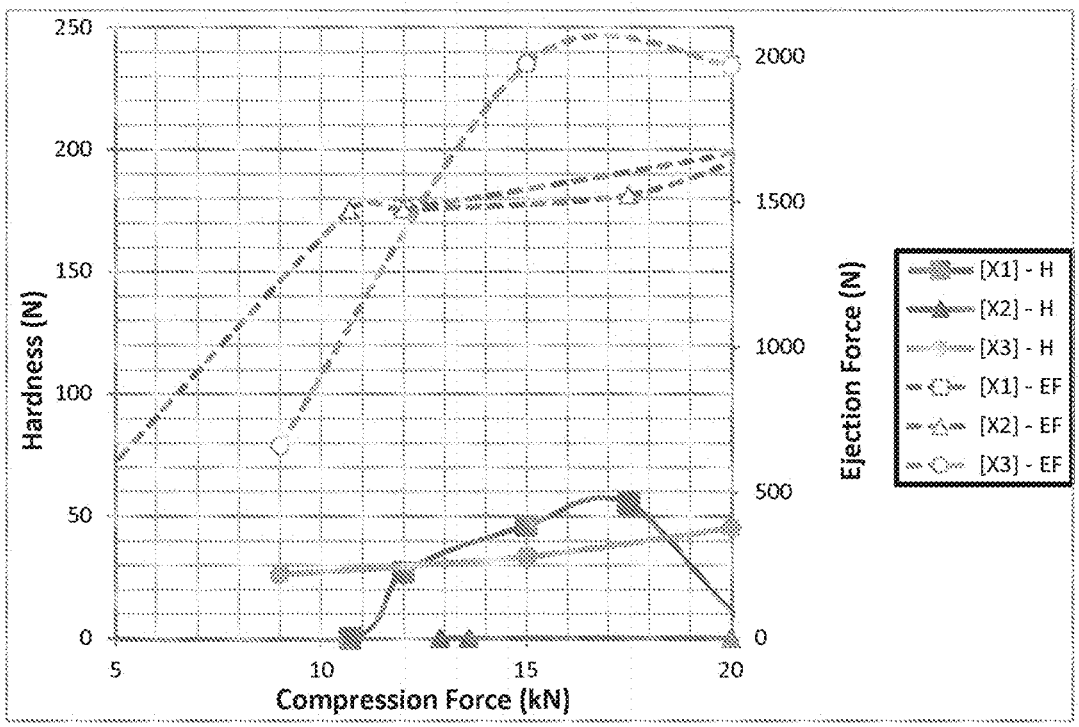

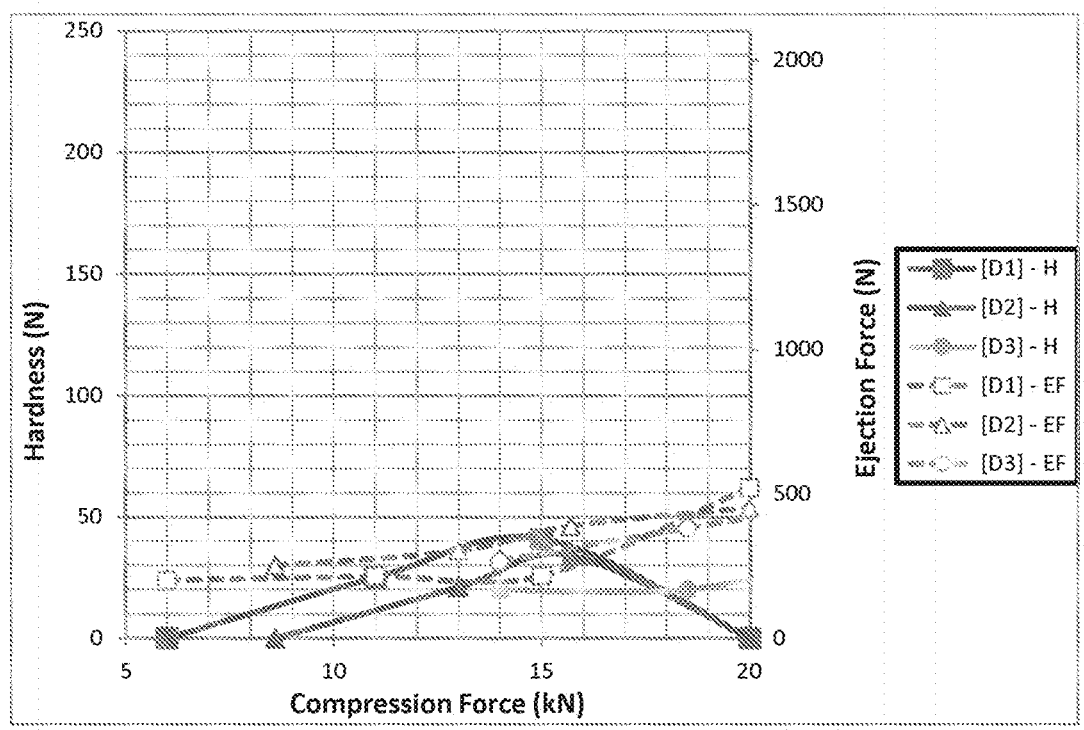

SUGAR COMPOSITIONS FOR TABLETING BY DIRECT COMPRESSION

The present invention relates to directly compressible compositions comprising more than 30% by weight of allulose, and to tablets obtainable thereof.

PRIOR ART

Allulose is a hexoketose monosaccharide sweetener, which is a C-3 epimer of D-fructose and is rarely found in nature. It has 70% relative sweetness but 0.3% energy of sucrose, and is suggested as an ideal sucrose substitute for food products. It shows important physiological functions, such as blood glucose suppressive effect, reactive oxygen species scavenging activity, and neuroprotective effect. It also improves the gelling behavior and produces good flavor during food process.

A non-cariogenic sweetener with a major component of allulose has been reported in literature to offer health benefits relevant to weight management and obesity related illnesses (i.e. type II diabetes, metabolic disorders).

Allulose has already been used as a sweetener in food and drink formulations, (see for instance patent applications EP 2 156 751 A1, US 2012/076908 A1 and US 2009/304891 A1), but could not be found in the form of tablets in the prior art.

However there would be a great advantage to have tablets based on allulose, i.e., tablets comprising great amount of allulose, for use as a sweetener with health related benefits in confectionary products as well as nutritional and dietary supplement. Human or vetenary pharmaceutical solid dosage form (tablets) could also take advantages of such excipient.

Over the past hundred years tablet manufacturers have developed materials and processes that can produce compressed tablets containing a precise amount of (active) ingredients, at high speed and at relatively low cost. Experts in the art of tableting are aware with the basic art of tableting by the three well-known methods, i.e. wet granulation, roller compaction and direct compression.

The simplicity of the direct compression process is apparent from a comparison of the steps involved in the manufacture of tablets by wet granulation, roller compaction and direct compression techniques (see for review, G. K. Dokala et al, Direct Compression—An Overview, *International Journal of Research in Pharmaceutical and Biomedical Sciences*, 4(1):155-158, 2013.).

The prime advantage of direct compression over wet granulation is economic since the direct compression requires fewer unit operations. This means less equipment, lower power consumption, less space, less time and less labor leading to reduced production cost of tablets.

Direct compression is more suitable for moisture and heat sensitive active ingredients, since it eliminates wetting and drying steps and increases the stability of active ingredients by reducing detrimental effects.

The tablets prepared by direct compression disintegrate into actives ingredient particles instead of granules that directly come into contact with dissolution fluid and exhibits comparatively faster dissolution.

The high compaction pressure involved in the production of tablets by slugging or roller compaction can be avoided by adopting direct compression.

Finally, materials are "in process" for a shorter period of time, resulting in less chance for contamination or cross contamination, and making it easier to meet the requirement of current good manufacturing practices.

Unfortunately, direct compression technic has the disadvantage of being extremely sensitive as regards to the nature and behavior of the direct compression excipient used.

First and logically, compressibility is required for satisfactory tableting, i.e., the mass must remain in the compact form once the compression force is removed. Hence, the directly compressible composition should allow the obtaining of tablets of sufficient hardness.

The directly compressible composition must tolerate significant compression force while keeping its integrity upon ejection from the tablet die. This means that the ejection force required after the application of the punch onto the powder to be compressed must be as low as possible. Indeed, the force applied onto the powder to form the compact generates adhesion of this compact to the metallic surface of the die and consequently frictions when the tablet is ejected from the die. These frictions can create scratches, surface damages, loss of matters and even tablets breaks. To produce entire and nice tablets it is necessary to restrict the frictions and consequently to have a low ejection force.

Also, a directly compressible composition should be free-flowing, should have high dilution potential, should be capable of being reworked without loss of flow or hardness, should remain unchanged chemically and physically, should have reproducible particle size distribution, should be compatible with other ingredients in the tablets and should have satisfactory color and taste.

These directly compressible compositions include various ingredients, usually:
- diluents, also called "direct compression excipients" for the reason that they are the major compounds in the tablets and are responsible for the flow properties and compressibility of the powder to be compressed;
- (super-) disintegrants, whose aim is to facilitate tablet disintegration in aqueous media, to promote the release of active ingredients, for instance when the tablet is ingested;
- lubricants, whose role is to enable the ejection of matrices, newly formed tablets;
- glidants, whose role is to promote the flow of the powder within the equipment;
- pH stabilizing agents, colorants, flavors, surfactants.

Commonly used directly compressible excipients are anhydrous lactose, cellulose and microcrystalline cellulose (MCC). Direct compression excipients are the major ingredients in these compositions, as their role and their quantities are of importance in these compositions. They must be in large amounts to allow the obtaining of a solid dosage form.

As a result, only a little amount of other material can usually be introduced in tablets. This is why tablets comprising great amounts of allulose could not be found in the prior art.

However, the inventors succeeded in obtaining tablets which can comprise more than 30% by weight of allulose.

To do so, the inventors prepared allulose capable of acting as a direct compression excipient, and as a result, that can be introduced in significant amounts in tablets. The allulose according to the invention can advantageously fill both roles of sweetener and direct compression excipient.

Indeed, allulose is not naturally compressible; meaning that allulose obtained by natural crystallization in water is not compressible. It lacks flow, cohesion or lubricating properties necessary for the production of tablets by direct compression.

There was no hint in the prior art suggesting tablets comprising significant amounts of allulose. There was no hint in the prior art suggesting allulose acting as a direct compression excipient.

OBJECTIVE

It was thus an object of the present invention to provide directly compressible compositions comprising significant amounts of allulose.

It was another object of the invention to provide tablets based on allulose, i.e. tablets exhibiting high amounts of allulose, and at the same time, satisfying hardness.

BRIEF DESCRIPTION OF THE INVENTION

In a first aspect, the invention is directed to the use of allulose as a direct compression excipient in a directly compressible composition.

In a second aspect, the invention provides allulose, particularly suitable for such use, which is compressible in the sole presence of a lubricant, to form a tablet having a diameter of 13 mm, a weight of 800+/−5 mg, a cylindrical shape with convex faces with a radius of curvature of 13 mm, whose hardness is greater than 50 N, at at least one compression force chosen within the range of 5 to 20 kN, the ejection force being lower than 1200 N.

In third aspect, the invention provides a directly compressible composition comprising allulose, wherein allulose represents at least 30% of said directly compressible composition, said percentage being expressed in dry weight, with respect to the total dry weight of said directly compressible composition.

In a fourth aspect, the invention provides a method for the manufacture of a tablet, comprising the steps of: providing a directly compressible composition according to the invention; followed by directly compressing the composition to form the tablet.

In a fifth aspect, the invention provides a tablet comprising allulose and wherein allulose represents at least 30% of said tablet, said percentage being expressed in dry weight, with respect to the total dry weight of said tablet.

BRIEF DESCRIPTION OF THE DRAWINGS

FIG. 1 shows measurement of compressibility and election force of compositions comprising allulose in Example 1.

FIG. 2 shows measurement of compressibility and election force of compositions comprising zylitol in Example 1.

FIG. 3 shows measurement of compressibility and election force of compositions comprising anhydrous dextrose in Example 1.

DETAILED DESCRIPTION OF THE INVENTION

The inventors succeeded in obtaining compositions based on allulose, suitable for direct compression, as evidenced in Examples 1, section 2), FIG. 1. These directly compressible compositions allowed the formation of tablets having great hardness, greater than 50 N, when compressed at satisfying compression forces which do not need to exceed 20 kN, and at the same time, satisfying ejection forces were measured. These compositions had high amounts of allulose, and no other compression excipient was required to obtain these results.

The inventors thus made it possible to obtain tablets comprising significant amounts of allulose, which can be greater than 30% by weight relative to the total weight of the tablet, typically of between 50 and 99%.

Allulose can advantageously play both role of direct compression excipient and low-calorie sweetener in these compositions.

This was not possible before the present invention, because compressible allulose could not be found. If high amounts of allulose would have been used, the compositions obtained thereof would have been impossible to compress.

A first object of the present invention is thus the use of allulose, as a direct compression excipient in a directly compressible composition.

In the present invention, "directly compressible composition" means a powdery composition suitable, per se, for the manufacture of tablets by direct compression. This composition always comprises a direct compression excipient or a mixture of direct compression excipients. Such a composition allows the manufacture of tablets of sufficient hardness, and of satisfying appearance.

Preferably, the allulose of the invention is further used as a sweetener, preferably as a low-calorie sweetener, i.e. for the manufacture of tablets having calorific value lower than 5 kcal/g, preferably lower than 4 kcal/g, preferably lower than 3 kcal/g, preferably lower than 2 kcal/g, even more preferably lower than 1 kcal/g.

It is preferably used as a sweetener having a relative sweetness, as compared to sucrose, of between 0.5 and 1.0, preferably of between 0.6 and 0.8, typically of 0.7.

Preferably, the allulose of the invention is further used as a health ingredient having physiological functions, such as blood glucose suppressive effect, reactive oxygen species scavenging activity, and/or neuroprotective effect.

A second object of the present invention is to provide allulose, particularly suitable for such use. This allulose is compressible in the sole presence of a lubricant, to form a tablet having a diameter of 13 mm, a weight of 800+/−5 mg, a cylindrical shape with convex faces with a radius of curvature of 13 mm, whose hardness is greater than 50 N, preferably greater than 60 N, preferably greater than 70 N, preferably greater than 80 N, preferably greater than 90 N preferably greater than 100 N, preferably greater than 110 N, even more preferably greater than 120 N, at at least one compression force ranging from 5 to 20 kN, the ejection force being lower than 1200 N, preferably lower than 1000 N, preferably lower than 600 N, even more preferably lower than 500 N.

In order to evaluate if a material is compressible and can allow forming tablets having the hardness complying with the invention, the person skilled in the art can adapt the nature and the amount of lubricant used. The material to be compressed can be for instance composed of 98.8% by weight of said material and 1.2% of lubricant, usually magnesium stearate.

The hardness can be evaluated by the person skilled in the art on a hardness tester. The value given in newtons usually corresponds to a mean value from 10 measurements.

The "hardness" and the "ejection force" can in particular be determined according to "Procedure 1" disclosed hereinafter in the Examples.

In a particular preferred embodiment of the invention, hardness is greater than 50 N, at compression forces ranging from 9 to 20 kN, preferably at compression forces ranging from 6 to 20 kN, In another particular preferred embodiment of the invention, hardness is greater than 50 N, preferably greater than 60 N, preferably greater than 70 N, preferably greater than 80 N, at compression forces ranging from 10 to 20 kN.

In another particular preferred embodiment of the invention, hardness is greater than 50 N, preferably greater than 60 N, preferably greater than 70 N, preferably greater than 80 N, preferably greater than 90 N, at compression forces ranging from 11 to 20 kN.

In another particular preferred embodiment of the invention, hardness is greater than 50 N, preferably greater than 60 N, preferably greater than 70 N, preferably greater than 80 N, preferably greater than 90 N, preferably greater than 100 N, at compression forces ranging from 12 to 20 kN or from 13 to 20 kN.

In another particular preferred embodiment of the invention, hardness is greater than 50 N, preferably greater than 60 N, preferably greater than 70 N, preferably greater than 80 N, preferably greater than 90 N, preferably greater than 100 N, preferably greater than 110 N at compression forces ranging from 14 to 20 kN, or from 15 to 20 kN, or from 16 to 20 kN.

In another particular preferred embodiment of the invention, hardness is greater than 50 N, preferably greater than 60 N, preferably greater than 70 N, preferably greater than 80 N, preferably greater than 90 N preferably greater than 100 N, preferably greater than 110 N, even more preferably greater than 120 N, at compression forces ranging from 17 to 20 kN, or from 18 to 20 kN, or from 19 to 20 kN.

In another particular preferred embodiment of the invention, hardness is greater than 50 N, preferably greater than 60 N, preferably greater than 70 N, preferably greater than 80 N, preferably greater than 90 N preferably greater than 100 N, preferably greater than 110 N, at a compression force of 15 kN, In general, the hardness is lower than 800 N, even lower than 700 N, even lower than 600 N, even lower than 500 N, even lower than 400 N, even lower than 300 N, even lower than 200 N, even lower than 150 N.

In general, the ejection force is greater than 50 N, even greater than 100 N, even greater than 200 N, even greater than 300 N.

The allulose according to the invention is preferably crystalline allulose, preferably obtained by crystallization in water or in a mixture of ethanol and water, preferably in water alone.

The allulose according to the invention preferably has mean volume diameter D 4,3 greater than 45 pm and equal to or lower than 310 µm, preferably equal to or lower than 250 µm, preferably equal to or lower than 200 µm, preferably equal to or lower than 125 µm.

The mean volume diameter D 3,4 can be determined by the person skilled in the art on a LASER diffraction granulometer type LS 230 from the company BECKMAN-COULTER, equipped with its powder dispersion module (dry method), following the manufacturers technical manual and specifications. The measurement range of the LASER diffraction granulometer type LS 230 is from 0.04 µm to 2000 µm. The operating conditions of hopper screw speed and intensity of vibration of the dispersion channel are determined in such a way that the optical concentration is between 4% and 12%, ideally 8%. The results are calculated in percentage by volume, and expressed in pm.

The allulose according to the invention preferably has a bulk density between 0.50 to 1.10 g/mL, preferably between 0.60 and 1.00 g/mL, preferably between 0.70 and 0.90 g/mL, even more preferably between 0.80 and 0.90 g/mL.

The allulose according to the invention preferably has a tapped density between 0.60 to 1.20 g/mL, preferably between 0.70 and 1.10 g/mL, preferably between 0.80 and 1.00 g/mL, even more preferably between 0.90 and 1.00 g/mL.

The bulk density and tapped density can in particular be determined by the person skilled in the art by graduate cylinder method (WHO Document QAS/11.450 FINAL, 2012).

Allulose according to the invention generally has purity equal to or greater than 90.0%, more specifically ranging from 90.0 to 99.8%, more specifically equal to or greater than 96.0%, more specifically equal to or greater than 98.0%, typically of between 98.0 and 99.8%.

The purity can in particular be determined by the person skilled in the art by using HPLC method with calcium column.

Allulose can be in either the D- or L-configuration, however D-allulose is preferred in the present invention, because easier to manufacture.

It is another object of the present invention to provide a directly compressible composition comprising a significant amount of allulose, notably without requiring the adding of other direct compression excipients.

In the directly compressible composition according to the invention, allulose represents at least 30%, preferably at least 40%, preferably at least 50%, preferably at least 60%, preferably at least 70%, preferably at least 80%, preferably at least 90%, typically between 90 and 99%, said percentage being expressed in dry weight, with respect to the total dry weight of said directly compressible composition.

Preferably, the directly compressible composition according to the invention comprises no more than 60%, preferably no more than 50%, preferably no more than 40%, preferably no more than 30%, preferably no more than 20%, preferably no more than 10%, preferably no more than 5%, more preferably no more than 2%, and most preferably 0% of direct compression excipient other than allulose, said percentage being expressed in dry weight with respect to the total dry weight of said directly compressible composition.

Preferably, the allulose of the directly compressible compositions according to the invention is such as described before, with all of its preferred embodiments.

It is another object of the present invention to provide a method for the manufacture of a tablet comprising the steps of: providing a directly compressible composition according to the invention; and directly compressing the composition to form the tablet.

It is another object of the present invention to provide a tablet comprising significant amounts of allulose, notably without requiring the presence of other direct compression excipients.

In the present invention, "tablet" shall mean any solid edible preparation, which is obtained by direct compression. These tablets can be in the form of suckable tablets like mints, or in the form of soft or hard chewable tablets. They can be normal or multi layers tablets. They can be used as a nutritional or dietary supplement, or as a pharmaceutical, and can be intended for humans, adults or children, or to animals.

In the tablet according to the invention, allulose represents at least 30%, preferably at least 40%, preferably at least 50%, preferably at least 60%, preferably at least 70%, preferably at least 80%, preferably at least 90%, typically between 90 and 99%, said percentage being expressed in dry weight with respect to the total dry weight of said tablet.

Preferably, the tablet comprises no more than 60% of compression excipient other than allulose, preferably no more than 50%, preferably no more than 40%, preferably no more than 30%, preferably no more than 20%, preferably no more than 10%, preferably no more than 5%, more preferably no more than 2%, and most preferably 0%, said percentage being expressed in dry weight, with respect to the total dry weight of said tablet.

Preferably the tablet is a sweet tablet, having calorific value lower than 5 kcal/g, preferably lower than 4 kcal/g, preferably lower than 3 kcal/g, preferably lower than 2 kcal/g, even more preferably lower than 1 kcal/g.

It preferably has a relative sweetness, as compared to sucrose, of between 0.5 and 1.0, preferably of between 0.6 and 0.8, for example of 0.7.

Preferably, the tablet according to the invention has hardness greater than 50 N, preferably greater than 60 N, preferably greater than 70 N, preferably greater than 80 N, preferably greater than 90 N, preferably greater than 100 N, preferably greater than 110 N, preferably greater than 120 N.

In general, the hardness of the tablet is lower than 800 N, even lower than 700 N, even lower than 600 N, even lower than 500 N, even lower than 400 N, even lower than 300 N, even lower than 200 N, even lower than 150 N.

Preferably, the allulose of the tablets according to the invention is such as defined before, with all its preferred embodiments.

The tablets according to the invention can be coated, notably by regular spray-drying of a film-forming composition onto a moving bed of tablets. The coating layer in general, does not exceed 5% by weight of the coated tablet. The tablets may also be coated with sugars or polyols, using a "sugar-coating" process to form a frosting or a soft or hard coating, depending on the amount of powders or the coating process used.

In the present invention, directly compressible compositions, as well as the tablets, generally comprise other ingredients. Such "other ingredients" can be without limitation:
- direct compression excipient other than allulose, for example (i) directly compressible sugar alcohols like directly compressible forms of sorbitol, mannitol, maltitol, xylitol, isomalt, lactitol, erythritol, (ii) directly compressible sugars like directly compressible forms of sucrose, dextrose, dextrates, lactose, (iii) microcrystalline cellulose, (iv) directly compressible minerals; however it is reminded that the composition for tableting by direct compression according to the present invention preferably comprises no more than 60%, and most preferably 0% of direct compression excipient other than allulose;
- dispersants or disintegrants, for example sodium starch glycolate, crosslinked carboxymethyl cellulose, crosslinked polyvinylpyrrolidone, chemically modified cellulose, starches;
- granulating agents such as polyvinyl pyrrolidone, chemically modified cellulose, gum acacia, dextrose, glucose syrup, gelatin, maltodextrin, starch and starch derivatives, gum tragacanth and the like;
- lubricants, for example magnesium stearate, stearic acid, sodium stearyl fumarate, sucroesters;
- food additives, such as flavoring agents, for instance mint, honey, essential oils such as citrus, peppermint or eucalyptus, fruit flavors, acidulants such as citric acid, acidity regulators;
- colorants like mineral dyes, pigments or solubles colorants;
- glidants (for example silica dioxide) or anti-sticking agent (for example talcum);
- pharmaceutical, nutraceutical or veterinary active substances;

and mixtures thereof.

It is another object of the present invention to provide a process, for the manufacture of allulose according to the invention, comprising:
- a step (a) of providing allulose obtained by crystallization in water or in a mixture of ethanol and water, preferably in water alone;
- a step (b) of grinding allulose obtained in step (a);
- a step (c) of sieving the allulose obtained in step (b), so as to obtain allulose having mean volume diameter D 4,3 greater than 45 μm and equal to or lower than 310 μm, preferably equal to or lower than 250 μm, preferably equal to or lower than 200 μm, preferably equal to or lower than 125 μm;
- a step (d) of recovering the allulose obtained in step (c).

For the step (a) of providing allulose obtained by crystallization in water or in a mixture of ethanol and water, the person skilled in the art will adapt the mean volume diameter D 4,3 of the allulose obtained, as a function of the mean volume diameter D 4,3 of the allulose to be recovered in step (d).

Preferably, the step (b) of grinding allulose is performed by a continuous dry mechanical grinding. Numerous mills are available for such grinding, for instance mills equipped with blades or with rotor/stator, squirrel cage mills, oscillating, conical or cylindrical sieve mills, hammer mills and so on.

The following Examples serve to illustrate the invention and should by no means be construed so as to limit the scope of the invention.

EXAMPLES

Example 1

Evaluation of Various Alluloses in Compositions for Tableting by Direct Compression In the following Examples, alluloses according to the invention were prepared.

Other carbohydrates used as sweeteners, xylitol and anhydrous dextrose, were also prepared for comparison.

These materials were then evaluated as direct compressible excipients.

To this end, tablets composed of the material to be tested as a directly compressible excipient and of a lubricant were prepared at various compression forces. The required ejection force to eject the tablets from their dies and the hardness of the tablets thus obtained were measured according to Procedure 1 below-described.

Procedure 1—Tablets Preparation and Hardness and Ejection Forces Measurements

Compositions composed of 98.8% by weight of the material to be tested as a directly compressible excipient and 1.2% by weight of magnesium stearate were first prepared. The material to be tested as a directly compressible excipient was mixed with magnesium stearate (Pharma Veg, specific grade of magnesium stearate marketed by Baerlocher Gmbh as a lubricant for the manufacture of tablets) in a TURBULA T2C mixer for 3 minutes.

Tablets were prepared out from these compositions, by means of Korsch XP1 (Korsh, Berlin, Germany) single punch tablet press using various compression forces varying from 4 to 25 kN.

These tablets had a diameter of 13 mm, a weight of 800+/−5 mg, a cylindrical shape with convex faces with a radius of curvature of 13 mm.

The ejection force, i.e. the force exerted by the lower punch on the tablet formed in the die to eject it, was measured by a wire strain jauge (full instrumentation package and PharmaResearch V1.0 installed on the press). So this value was directly given by the PharmaResearch data software installed on the press.

The inventors then measured the hardness of the tablets thus obtained on a hardness tester (Dr. Schleuniger Pharmatron Model 6). The value given in Newtons corresponds to a mean value from 10 measurements.

1) Preparation of Alluloses and Comparative Carbohydrates a) Preparation of Allulose According to the Invention An allulose syrup was first prepared as follow: a crystalline fructose with purity about 99% was dissolved in water to about 45% dry substance. The syrup was allowed to react with an epimerization enzyme at 55.0° C., regulated pH of 7.0. After 40 hours of reaction, the syrup sample was collected. The resulted syrup has 25.2% allulose and 74.8% fructose using standard HPLC method. This syrup was passed through microfiltration to remove insoluble cell mass of enzyme, then carbon filtration to remove color, and then demineralization on cation and anion ion exchange column to further remove minerals and other impurities. The syrup was then concentrated to a dry solid of about 60% using conventional evaporator. Concentrated allulose syrup at 25.2% with above steps was passed through a simulated moving bed chromatograph column (SMB) with calcium form resin. The resulted syrup had an allulose content of 93%.

Allulose syrup obtained from above steps was further concentrated to 85% dry substance using a conventional evaporator. It was then fed into a pilot batch cooling crystallizer to produce crystalline allulose. The crystallization conditions were 50° C. at the start of crystallization and 20° C. for 90 hours.

Crystals from crystallizer were centrifuged at 1700 rpm. The resulted crystals were then dried using fluidized bed ramping from 25° C. to 90° C. and then to 25° C. with total time of 4 hours.

Crystalline allulose thus obtained was grinded using a Universal Mill M20 (IKA, Staufen, Germany) and then sieved in a sieve sequence from bottom to top as follows: 45 μm, 125 μm, 250 μm and 310 μm. Three cuts were thus obtained, having particle size (Ø) ranging within the ranges of:

45 μm<Ø≤125 μm, i.e. having mean volume diameter D 4,3 greater than 45 μm and equal to or lower than 125 μm (allulose [A1]);

125 μm<Ø≤250 μm i.e. having mean volume diameter D 4,3 greater than 125 μm and equal to or lower than 250 μm (allulose [A2]);

250 μm<Ø≤310 μm i.e. having mean volume diameter D 4,3 greater than 250 μm and equal to or lower than 310 μm (allulose [A3]);

These three alluloses were put into the form of tablets and evaluated for hardness (H) and ejection force (EF) according to Procedure 1. The results are presented in FIG. 1.

b) Preparation of Xylitol

Crystal xylitol was obtained from Roquette commercial production with mean particle size of 500 μm. The crystal product was grinded and sieved in the same way as for allulose.

Three cuts [X1], [X2] and [X3] were thus obtained, having same particle size as allulose [A1], [A2] and [A3] respectively.

These three xylitols were put into the form of tablets and evaluated for hardness (H) and ejection force (EF) according to Procedure 1. The results are presented in FIG. 2.

c) Preparation of Anhydrous Dextrose

Crystal anhydrous dextrose was obtained from Roquette commercial production with mean particle size of 300 μm. The crystal product was grinded and sieved in the same way as for allulose.

Three cuts [D1], [D2] and [D3] were thus obtained, having same particle size as allulose [A1], [A2] and [A3] respectively.

These three anhydrous dextroses were put into the form of tablets and evaluated for hardness (H) and ejection force (EF) according to Procedure 1. The results are presented in FIG. 3.

2) Results: Evaluation for Tableting by Direct Compression

In FIGS. 1 to 3:

"H" means Hardness; hardness equal to 0, means that the tablet broke during compression.

"EF" means Ejection Force.

Unlike other sweetener, and despite its similarities in terms of crystalline shape and density, allulose was found to be directly compressible in its crystalline state.

Great compressibilities and ejection forces were obtained with the use of allulose having mean particle diameter D 4,3 between 45 and 250 μm.

Best compressibilities and at the same time, ideal ejection forces, were obtained with the use of an allulose having mean particle diameter D 4,3 between 45 and 125 μm.

These results cannot be obtained with other carbohydrates, as evidenced with the results obtained with xylitol or anhydrous dextrose.

Crystalline xylitol is not compressible even when grinded to smaller particles.

The inventors also tried to compress allulose and the other carbohydrates of prior art, before the step of grinding. The results are not presented in the Figures above, because none of the crystalline carbohydrates obtained before grinding was found compressible.

The invention claimed is:

1. A directly compressible composition comprising allulose as a direct compression excipient.

2. The directly compressible composition of claim 1, wherein the allulose is present in an amount effective to be used as a sweetener.

3. The directly compressible composition of claim 1, wherein the allulose is present in an amount effective to be used as a health ingredient providing physiological functions selected from the group consisting of blood glucose suppressive effect, reactive oxygen species scavenging activity, and neuroprotective effect.

4. Allulose which is compressible in the sole presence of a lubricant, to form a tablet having a diameter of 13 mm, a weight of 800+/−5 mg, a cylindrical shape with convex faces with a radius of curvature of 13 mm, whose hardness is greater than 50 N at at least one compression force ranging from 5 to 20 kN, the ejection force being lower than 1200 N.

5. The allulose of claim 4, wherein said allulose is crystalline allulose.

6. The allulose according to claim 4, wherein said allulose has mean volume diameter D 4,3 greater than 45 μm and equal to or lower than 310 μm.

7. The allulose according to claim 4, wherein said allulose has a bulk density between 0.50 to 1.10 g/mL.

8. The allulose according to claim 4, wherein said allulose has a tapped density between 0.60 to 1.20 g/mL.

9. A directly compressible composition comprising allulose, wherein said allulose represents at least 30% of said directly compressible composition, said percentage being expressed in dry weight with respect to the total dry weight of said directly compressible composition.

10. The directly compressible composition of claim 9, comprising no more than 60% of direct compression excipient other than allulose, said percentage being expressed in dry weight, with respect to the total dry weight of said directly compressible composition.

11. A method for the manufacture of a tablet, comprising the steps of:
providing a directly compressible composition according to claim 9; and
directly compressing the composition to form the tablet.

12. A tablet comprising allulose, wherein allulose represents at least 30% of said tablet, said percentage being expressed in dry weight with respect to the total dry weight of said tablet.

13. The tablet of claim 12, wherein said tablets comprises no more than 60% of direct compression excipient other than allulose, said percentage being expressed in dry weight with respect to the total dry weight of said tablet.

14. The tablet according to claim 12, having hardness greater than 50 N.

15. A process for the manufacture of allulose of claim 4, comprising:
a step (a) of providing allulose obtained by crystallization in water or in a mixture of ethanol and water;
a step (b) of grinding allulose obtained in step (a);
a step (c) of sieving the allulose obtained in step (b), so as to obtain allulose having mean volume diameter D 4,3 greater than 45 µm and equal to or lower than 310 µm;
a step (d) of recovering the allulose obtained in step (c).

16. The allulose of claim 4 which is compressible in the sole presence of a lubricant, to form a tablet having a diameter of 13 mm, a weight of 800+/−5 mg, a cylindrical shape with convex faces with a radius of curvature of 13 mm, whose hardness is greater than 120 N, at at least one compression force ranging from 5 to 20 kN, whose the ejection force being lower than 500 N.

17. The allulose of claim 5, wherein said allulose is crystalline allulose obtained by crystallization in water or in a mixture of ethanol and water.

18. The allulose according to claim 6, wherein said allulose has mean volume diameter D 4,3 equal to or lower than 250 µm.

19. The allulose according to claim 6, wherein said allulose has mean volume diameter D 4,3 equal to or lower than 125 µm.

20. The directly compressible composition of claim 9, wherein allulose represents at least 90%, said percentage being expressed in dry weight with respect to the total dry weight of said directly compressible composition.

21. The directly compressible composition of claim 10, comprising no more than 10% of direct compression excipient other than allulose, said percentage being expressed in dry weight, with respect to the total dry weight of said directly compressible composition.

22. The directly compressible composition of claim 20, comprising no more than 10% of direct compression excipient other than allulose, said percentage being expressed in dry weight, with respect to the total dry weight of said directly compressible composition.

23. The tablet of claim 12, wherein allulose represents at least 90% of said tablet, said percentage being expressed in dry weight with respect to the total dry weight of said tablet.

24. The tablet of claim 13, wherein said tablets comprises no more than 10% of direct compression excipient other than allulose, said percentage being expressed in dry weight with respect to the total dry weight of said tablet.

25. The tablet of claim 23, wherein said tablets comprises no more than 10% of direct compression excipient other than allulose, said percentage being expressed in dry weight with respect to the total dry weight of said tablet.

26. Allulose which is directly obtained by the process of claim 15.

* * * * *